(12) United States Patent
Wollenweber

(10) Patent No.: US 6,917,666 B2
(45) Date of Patent: Jul. 12, 2005

(54) SYSTEM AND METHOD FOR TABLE/GANTRY ALIGNMENT IN IMAGING SYSTEMS

(75) Inventor: Scott David Wollenweber, Waukesha, WI (US)

(73) Assignee: General Electric Company, Schenectady, NY (US)

(*) Notice: Subject to any disclaimer, the term of this patent is extended or adjusted under 35 U.S.C. 154(b) by 201 days.

(21) Appl. No.: 10/323,255

(22) Filed: Dec. 19, 2002

(65) Prior Publication Data

US 2004/0120467 A1 Jun. 24, 2004

(51) Int. Cl.⁷ .................................................. A61B 6/08
(52) U.S. Cl. .......................................... 378/20; 378/206
(58) Field of Search ................................ 378/162, 204, 378/205, 206, 207, 209, 20; 600/407, 410, 411, 415, 417, 425, 429, 436

(56) References Cited

U.S. PATENT DOCUMENTS

| 4,117,337 A | * | 9/1978 | Staats | 378/17 |
| 4,242,587 A | * | 12/1980 | Lescrenier | 378/20 |
| 4,296,329 A | * | 10/1981 | Mirabella | 250/491.1 |
| 4,538,289 A | * | 8/1985 | Scheibengraber | 378/20 |
| 4,717,251 A | * | 1/1988 | Wells et al. | 356/4.08 |
| 5,204,629 A | | 4/1993 | Ueyama | 324/318 |
| 5,255,680 A | | 10/1993 | Darrow et al. | 600/424 |
| 5,622,187 A | | 4/1997 | Carol | 128/897 |
| 5,675,625 A | * | 10/1997 | Rockseisen | 378/206 |
| 6,044,291 A | * | 3/2000 | Rockseisen | 600/429 |
| 6,229,869 B1 | | 5/2001 | Hu | 378/4 |
| 6,449,330 B1 | | 9/2002 | Li et al. | 378/4 |
| 6,449,331 B1 | | 9/2002 | Nutt et al. | 378/19 |
| 6,456,684 B1 | * | 9/2002 | Mun et al. | 378/20 |

* cited by examiner

Primary Examiner—Allen C. Ho
(74) Attorney, Agent, or Firm—Hunton & Williams

(57) ABSTRACT

In an imaging system including a gantry having a patient bore, and a patient table having a cradle, a method of aligning the cradle with a scan plane in the patient bore is disclosed. The method comprises positioning a laser device at least partially within the patient bore, the laser device producing an alignment laser beam projecting along a center axis of the patient bore normal to the scan plane. The method further comprises aligning the cradle of the patient table such that when the cradle is translated into the scan plane in the patient bore, the alignment laser beam intersects a positioning target on the cradle.

18 Claims, 5 Drawing Sheets

SYSTEM AND METHOD FOR TABLE/GANTRY ALIGNMENT IN IMAGING SYSTEMS

BACKGROUND OF THE INVENTION

The invention relates generally to systems and methods for aligning the patient table and gantry in medical imaging systems.

For imaging systems, such as Positron Emission Tomography (PET) and Computed Tomography (CT) imagers, the alignment of a patient within the imaging area can be very important to the success of the imaging. Without correct placement of the patient in the scanning field of view, the imagers will gather data that is not properly aligned, leading to inaccurate images.

In PET imaging systems, these issues often arise when performing a multiple axial field of view (AFOV) study. In PET-CT studies, similar issues arise between the CT and PET scans. PET is a procedure that allows a physician to examine the heart, brain, and other organs, by producing images that show the molecular functioning of an organ or tissue. PET imagers include, among other components, a patient table with a cradle, a gantry and an operating workstation. In operation, the patient is placed in the cradle and driven into the gantry patient bore where the imaging takes place. The patient bore is lined by a series of detector rings that gather imaging data when the scanner is imaging. The detector rings typically utilize thousands of scintillator crystals to measure coincidence events when radiation is released into the scanning field of view. The data gathered is used to produce an image of the patient's body. In a multiple-AFOV study, where several snapshots of different regions of a patient's body are put together to get a complete image of the imaged region, when the patient is not aligned correctly on the cradle with respect to the detector rings, the image will show visible discontinuities, often at the axial field overlap regions.

Accordingly, there is a need for a more efficient and accurate method of aligning the table and gantry of an imaging system. The invention provides a method of aligning the table and gantry of an imaging system, as well as an imaging system with alignment features, that overcome the disadvantages of known systems and methods while offering features not present in known systems and methods.

BRIEF SUMMARY OF THE INVENTION

In accordance with one embodiment of the invention, in an imaging system including a gantry having a patient bore, and a patient table having a cradle, a method of aligning the cradle with a scan plane in the patient bore is disclosed. The method comprises positioning a laser device within the patient bore, the laser device producing an alignment laser beam projecting along an axis of the patient bore normal to the scan plane. The method further comprises aligning the cradle of the patient table such that when the cradle is translated into the scan plane in the patient bore, the alignment laser beam intersects a positioning target on the cradle, for example.

In yet another embodiment of the invention, in an imaging system including a gantry having a patient bore, and a patient table having a cradle, a method of aligning the cradle with a scan plane in the patient bore is disclosed. The method comprises positioning a laser device at least partially within the patient bore, the laser device producing an alignment laser beam projecting along an axis of the patient bore normal to the scan plane, advancing the cradle into the patient bore, and repeatedly determining that the alignment laser beam intersects a cradle target on the cradle when the cradle is being advanced into the patient bore, for example.

An imaging system, according to one embodiment of the invention, comprises a gantry including a patient bore, a patient table including a cradle, and a laser device configured to produce an alignment laser beam projecting along an axis of the patient bore normal to a scan plane, wherein the alignment laser beam is configured to intersect a positioning target on the cradle such that the cradle is normal to the scan plane when the cradle is translated into the patient bore, for example.

BRIEF DESCRIPTION OF THE DRAWINGS

The present invention can be more fully understood by reading the following detailed description of the presently preferred embodiments together with the accompanying drawings, in which like reference indicators are used to designate like elements, and in which.

DETAILED DESCRIPTION OF THE INVENTION

In an imaging system including a gantry having a patient bore, and a patient table having a cradle, a method of aligning the cradle with a scan plane in the patient bore is disclosed. The method comprises positioning a laser device relative to the patient bore, the laser device producing an alignment laser beam projecting along an axis of the patient bore normal to the scan plane. The method further comprises aligning the cradle of the patient table such that when the cradle is translated into the scan plane in the patient bore, the alignment laser beam intersects a target point on a positioning target on the cradle.

Figure 1:
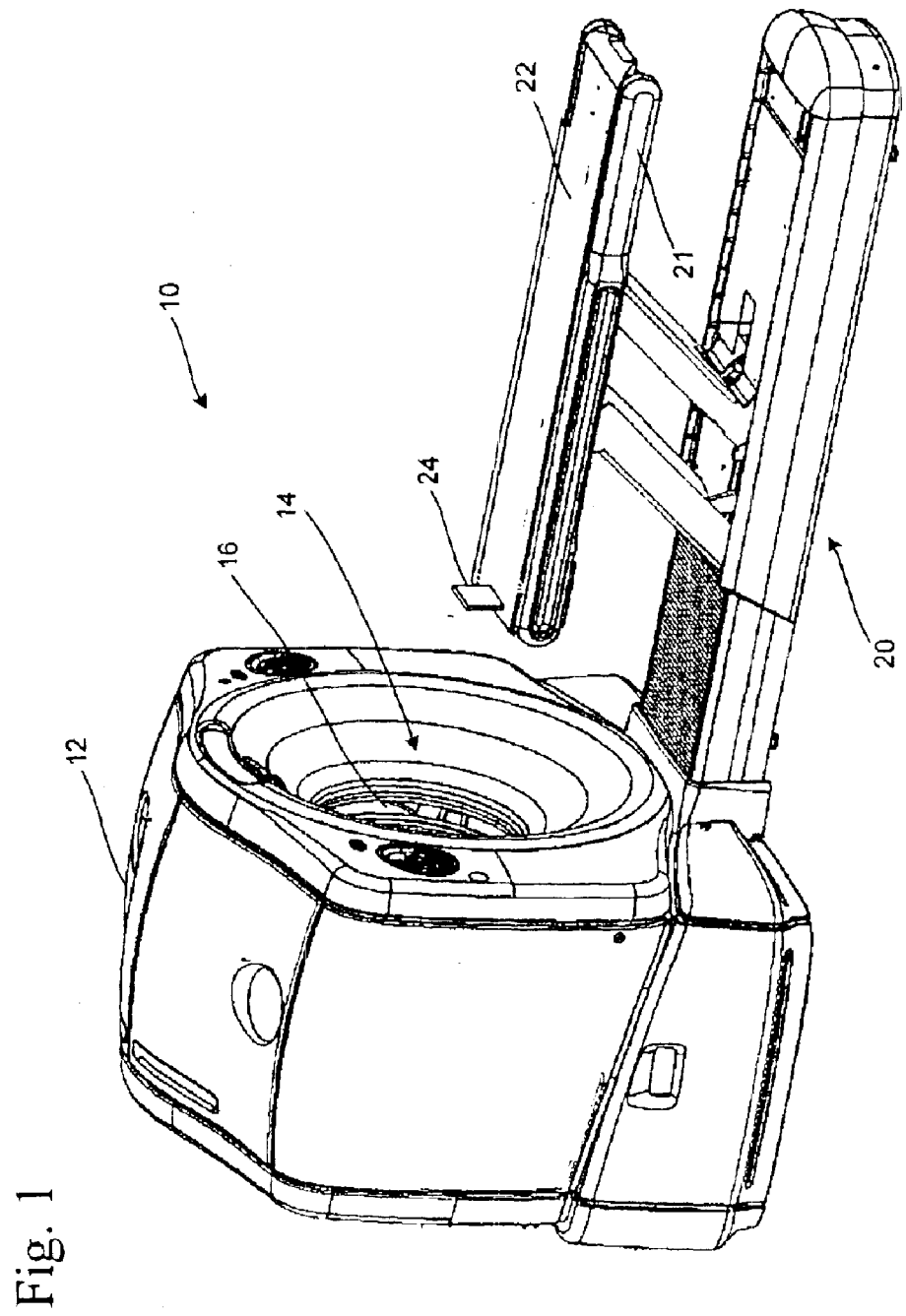
FIG. 1 is a perspective view of an imaging system in accordance with one embodiment of the invention.

FIG. 1 is a perspective view of an imaging system in accordance with one embodiment of the invention. Imaging system 10 includes gantry 12, patient table 20 and an operator workstation (not illustrated). The operator workstation typically commands and controls the processes and mechanical operation of the imaging system.

As shown in FIG. 1, gantry 12 has a patient bore 14 formed therein. The patient bore 14 is at least partially defined by the internal perimeter of detector ring assembly 16. It should be appreciated that many additional imaging system components, not shown in the figures, may be housed within gantry 12. Although imaging system 10, as shown in FIG. 1, is a combined PET and CT scanner, imaging system 10 may be a system that is capable of performing only PET, CT or other similar functions, for example.

Patient table 20 includes a patient cradle 22, which is adapted for having a patient resting thereon during use of imaging system 10. Patient table 20 is configured with a mechanical base 21 such that patient cradle 22 may be translated, or moved, into patient bore 14 such that a patient can be scanned by PET and CT detectors positioned in the detector ring assembly 16. Patient table 20 can typically be controlled to change the front and rear elevation of cradle 22, or alternatively, base 21 can be adjusted to alter the height of the cradle 22, for example.

Figure 2:
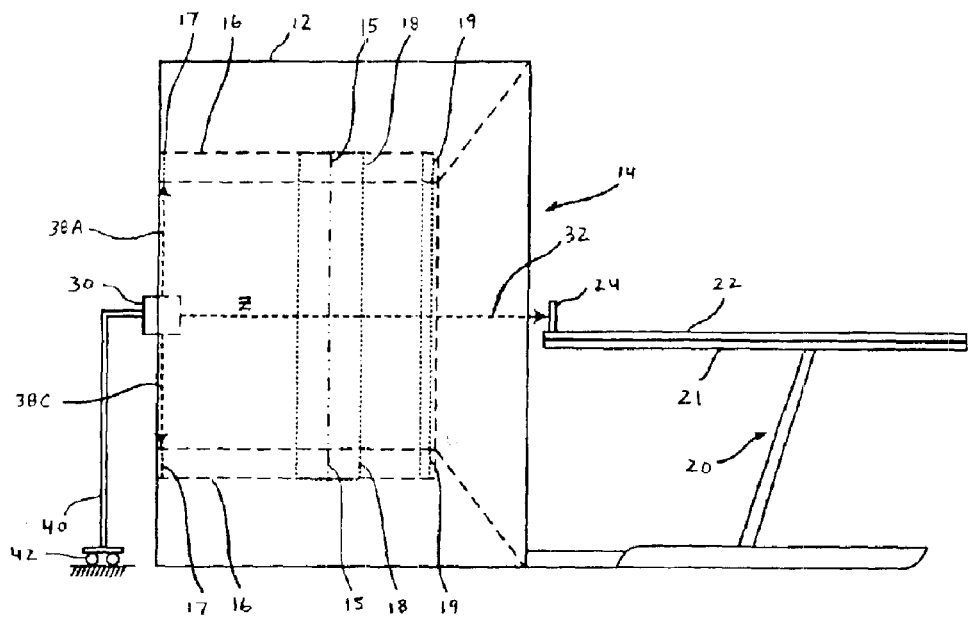
FIG. 2 is a side view of the imaging system of FIG. 1 in accordance with one embodiment of the invention.

FIG. 2 is a side view of the imaging system of FIG. 1 in accordance with one embodiment of the invention. As shown in FIG. 2, PET detectors positioned within detector ring assembly 16 capture data in the PET axial field of view (AFOV)18, while CT detectors positioned with detector ring assembly 16 capture data in the CT AFOV 19. Throughout the PET AFOV 18 and CT AFOV 19, there are many scan planes that when combined produce an image of an object being scanned, i.e., a section of a patient's body. As shown in FIG. 2, scan plane 15 is a plane located between the ends of the PET AFOV 18, and can be determined by reference to any well-defined axial plane of the detector ring assembly 16 within the PET AFOV 18. For example, the scan plane 15 may be defined by an individual detector ring within detector ring assembly 16 that captures data in PET AFOV 18, or by septa located within the PET AFOV 18 in detector ring assembly 16. The septa may be 1 mm thick partitions between individual detector rings, for example. Thus, it should be appreciated that while there are many scan planes in both AFOV 18 and 19, only scan plane 15 is shown for purposes of illustrating the invention. The combination of several images in a clinical AFOV study is described in further detail below with reference to FIGS. 3–4.

Referring to FIG. 2, laser device 30 is secured to a mount 40 and positioned at least partially within the patient bore 14 of gantry 12. Mount 40 may utilized to position laser device 30 within patient bore 14 when alignment is needed, and to remove laser device 30 from within patient bore 14 when the cradle 22 is stationary before scanning begins. In this embodiment, mount 40 is an adjustable flex-frame stand, with wheels 42 for rolling movement on the floor surface.

Laser device 30 is configured for producing a plurality of laser beams (produced in the X, Y and Z directions) used to properly align the cradle 22 relative to scan plane 15 within patient bore 14. An illustrative example of a laser device configured to produce laser beams in the described configuration is detailed in published U.S. application No. 2002/0054433, now U.S. Pat. No. 6,542,304, entitled "Laser Beam Device with Apertured or Non-Apertured Reflective Element."

According to one embodiment of the invention, the movement of patient cradle 22 can be characterized by reference to a cradle drive vector indicating the direction in the X, Y and Z directions that cradle 22 is moving. To reduce discontinuities in the resultant imaging, cradle 22, and the cradle drive vector, can be aligned normal to the scan plane 15, or alternatively, a correction may be utilized when producing the resultant imaging.

Figure 3:
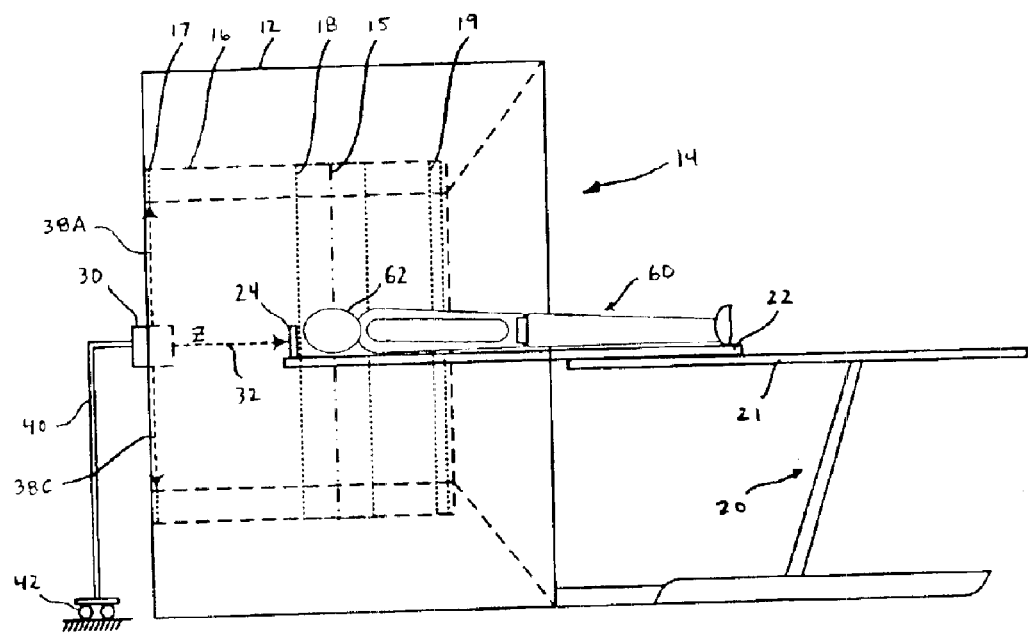
FIGS. 3 and 4 are side views of an illustrative patient in an imaging system in accordance with one embodiment of the invention.
Figure 4:
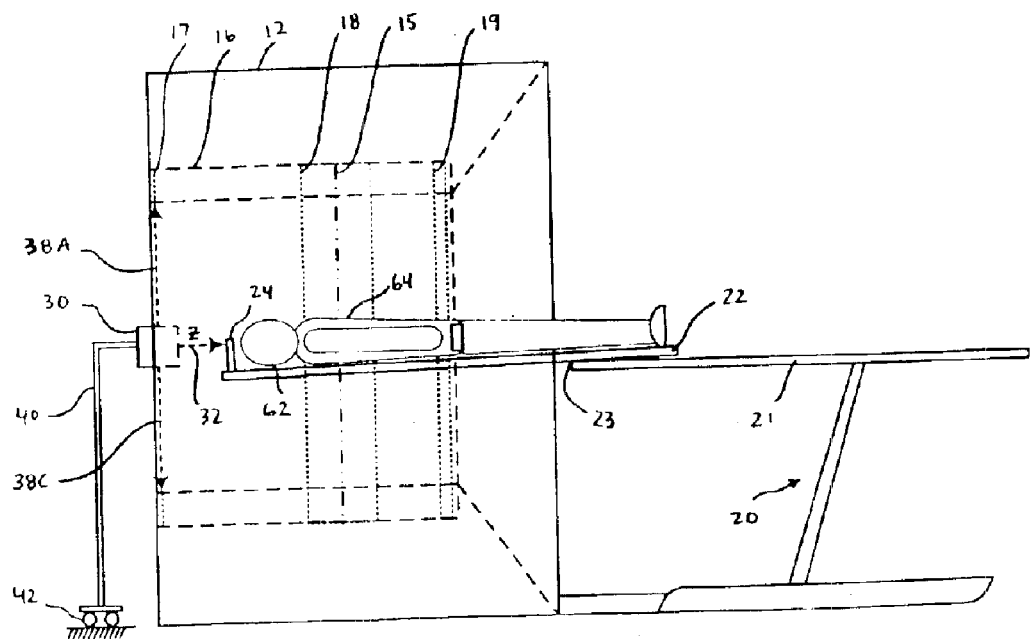

FIGS. 3 and 4 are side views of an illustrative imaging system in which an illustrative patient has been positioned in the patient bore for scanning in accordance with one embodiment of the invention. As shown in FIG. 3, a patient 60 has been translated into patient bore 14 to place the patient within the PET AFOV 18 or CT AFOV 19. Illustratively, in this embodiment, patient 60 is undergoing a multiple AFOV PET study which requires multiple snapshots of portions of the patient's body. To complete the study, the multiple snapshots are combined into an axial imageset. As shown in FIG. 3, the head and neck region 62 of patient 60 is within PET AFOV 18. Once the PET imaging data is collected for the head and neck region 62, the upper torso region 64 is placed within the PET AFOV 18 by translating the cradle 22 forward into patient bore 14, as shown in FIG. 4. The extension of cradle 22 into patient bore 14 combined with the weight of patient 60 can cause the cradle 22 to bend downwardly around fulcrum point 23 over the front edge of base 21, in a manner different from when the same axial portion of the patient was imaged previously in the PET AFOV 18 or CT AFOV 19. Without appropriate correction, when the two sets of imaging data from the head and neck region 62 and upper torso region 64 are combined, overlap regions would include discontinuities because of the vertical displacement of cradle 22 and patient 60, as a function of cradle translation into the patient bore 14.

Accordingly, to align the cradle 22 perpendicular to scan plan 15 in PET AFOV 18, laser device 30 produces an alignment laser beam 32 that is configured to intersect a target point 26 on a positioning target 24 positioned on cradle 22. As the cradle 22 is translated forward into the patient base 14 to image different regions of the patient 60, the system 10 determines whether the beam 32 is intersecting target point 26, and if not, measuring the displacement in the ±X and ±Y directions from target point 26. The displacement from the target point 26 can be utilized to realign the positioning of the cradle 22 during clinical operation, or apply the appropriate correction in the back projection process. Other sources of cradle misalignment that may be corrected using similar methods include misalignment of the cradle drive vector (i.e., not perpendicular to the scan plan in either X, Y transverse plane), mechanically related misalignment due to the table, cradle or other drive mechanisms for translating the cradle into the patient bore (i.e., rollers, tracks, or debris on either), for example.

Figure 5:
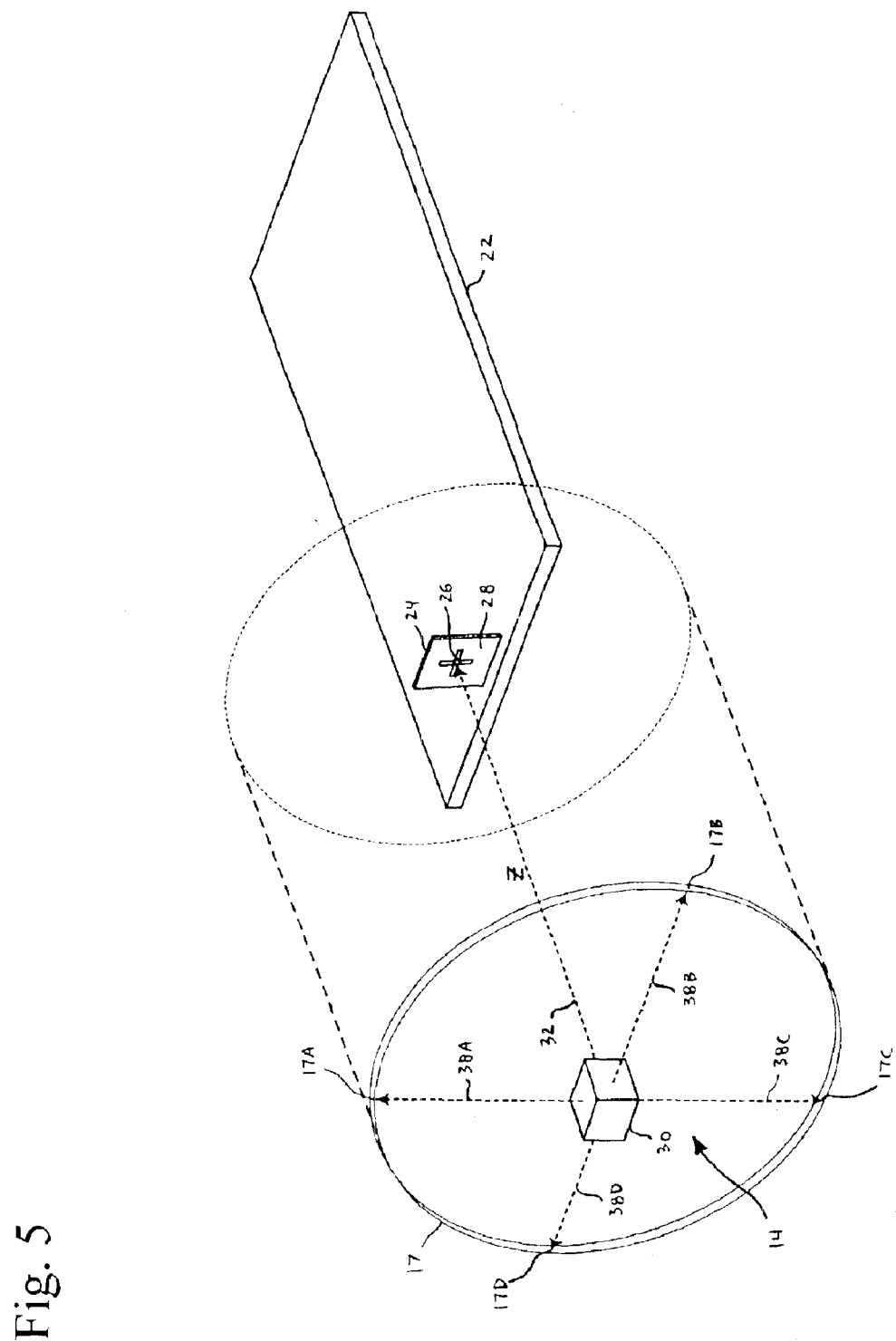
FIG. 5 is a perspective view of a laser device positioned in a patient bore for alignment with a positioning target located on a cradle in accordance with one embodiment of the invention.
Figure 6:
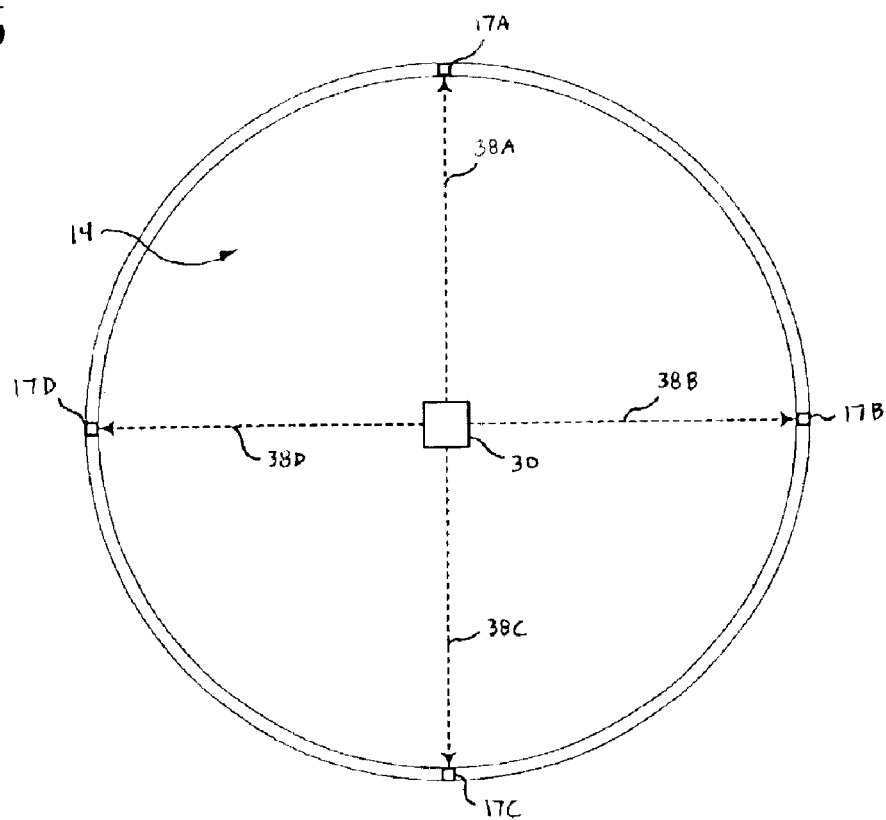
FIG. 6 is a planar view of a positioning septum and laser device in accordance with one embodiment of the invention.

FIG. 5 is a perspective view of laser device 30 positioned in patient bore 14 for alignment with positioning target 24 located on cradle 22 in accordance with one embodiment of the invention. To achieve proper alignment of the cradle 22 normal to the scan plane 15 (not illustrated in FIG. 5) and septum 17, the alignment laser beam 32 produced by laser device 30 is projected along an axis Z of the patient bore 14, typically the center axis. Laser device 30 is also configured to produce a plurality of coplanar laser beams 38A, 38B, 38C and 38D, each perpendicular to the alignment laser beam 32. Laser device 30 may be positioned at least partially within the patient bore 14 such that coplanar beams 38A–38D occupy the same plane. As shown in FIG. 6, each of the beams 38A–38D intersect an associated positioning point 17A–17D located on a septum 17. The plane occupied by beams 38A–38D and septum 17 is parallel to scan plane 15, shown in FIGS. 2 and 8 below. Accordingly, when beams 38A–38D intersect the associated positioning points 17A–17D on septum 17, alignment laser beam 32 is normal to the scan plane 15.

FIG. 6 is a planar view of a positioning septum 17 and laser device 30 in accordance with one embodiment of the invention. As shown in FIG. 6, beam 38A produced by laser device 30 intersects positioning point 17A on septum 17. Beam 38B intersects associated positioning point 17B, beam 38C intersects point 17C, and beam 38D intersects point 17D. In each circumstance, beams 38A–38D produce a laser dot on the associated positioning point 17A–17D, respectively, to confirm that beams 38A–38D are in a plane parallel to the scan plan 15 and normal to the alignment laser beam 32. A laser sensing device may be utilized on septum 17 at each point 17A–17D to determine that each beam 38A–38D are intersecting points 17A–17D.

It should be appreciated that although beams 38A–38D are perpendicular to each other as shown in FIG. 6, this configuration is not necessary. In further embodiments, for example, laser device 30 may produce any number of coplanar beams that intersect the septum 17 at varying angles wherein the plane they exist in is parallel to the scan plan 15.

Figure 7:
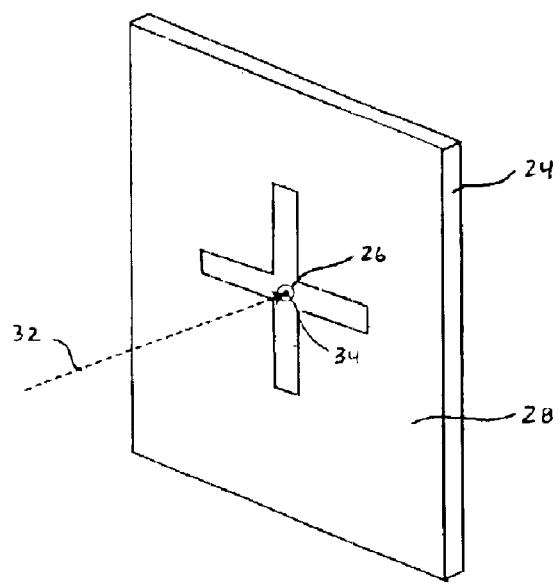
FIG. 7 is a perspective view of a positioning target in accordance with one embodiment of the invention.

FIG. 7 is a perspective view of positioning target 24 in accordance with one embodiment of the invention. In this embodiment, a laser sensing device 28 is affixed to the face of the positioning target 24. Laser sensing device 28 provides a target region, the focus of which is target point 26. Laser sensing device 28 may comprise a charge coupled device (CCD), which is an array of light sensor pixels that can be used to detect the position of a laser beam produced in the target region on the surface of the laser sensing device 28. According to one embodiment of the invention, beam 32 intersects the target point 26 on laser sensing device 28 and produces a laser dot 34. The system 10 gathers the data obtained by the laser sensing device 28 for determining the alignment of the cradle 22 relative to the scan plane 15. As shown in FIG. 7, target point 26 is the focus of a crosshair. When properly aligned, laser dot 34 is produced in the center of target point 26. The alignment of cradle 22 and scan plane 15 may be determined by measuring the distance away from the center of target point 26 by laser sensing device 28, allowing the user to determine the amount of correction needed for proper alignment.

As shown in FIG. 5, the positioning target 24 is positioned near the front of cradle 22 to allow a patient to be resting on the cradle 22 while alignment is verified. It should be appreciated that the positioning target 24 may be placed in any suitable located on cradle 22 that allows the user to verify that the laser alignment beam 32 intersects the target point 26, or otherwise determine the variation between laser dot 34 and target point 26. Although shown as a separate component in this embodiment, the positioning target 24 may be temporarily affixed to, permanently secured to or formed integrally as a part of the cradle 22. Instead of the positioning target 24, the target point may also be placed directly on some portion of the cradle 22.

Figure 8:
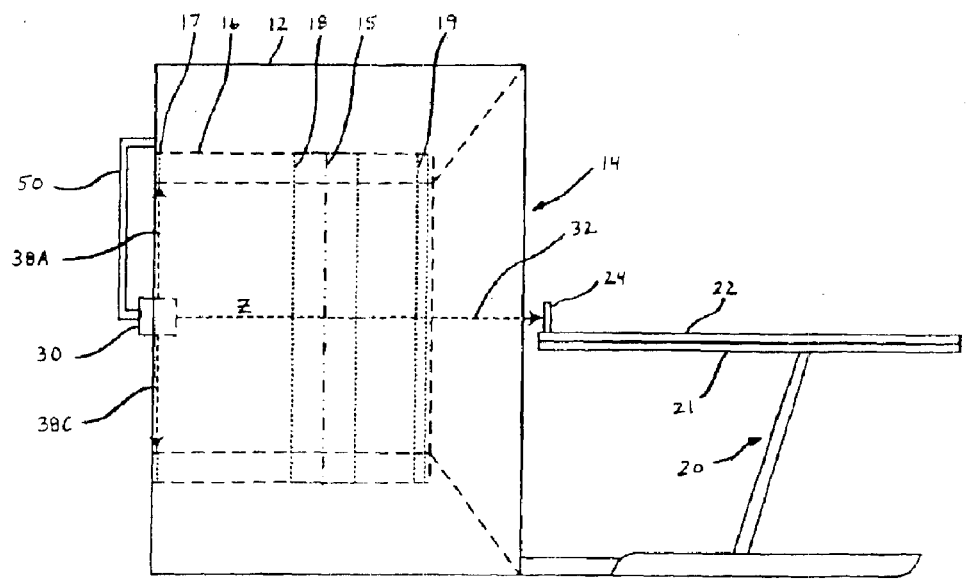
FIG. 8 is a side view of an imaging system in accordance with one embodiment of the invention.

FIG. 8 is a side view of an imaging system in accordance with one embodiment of the invention. As shown in FIG. 8, imaging system 10 includes many identical components as shown and described with reference to FIG. 2. However, in the embodiment shown in FIG. 8, laser device 30 is attached to an adjustable mount 50, the adjustable mount 50 allowing the user to position the laser device 30 within the patient bore 14 as necessary for alignment of the cradle 22 and scan plane 15. Adjustable mount 50 may utilized to position laser device 30 within patient bore 14 when alignment is needed, and to remove laser device 30 from within patient bore 14 when the cradle 22 is stationary before scanning begins.

Although the various embodiments of the invention illustrate ways to mount the laser device 30 and position the laser device 30 within the patient bore 14 for alignment, any suitable mount that is adjustable for properly aligning the laser device beams and which does not cause interference with the imaging may be utilized.

FIGS. 1–8 illustrate various embodiments of the invention in which a laser device is utilized to align the cradle of patient table and the scan plane of a gantry in an imaging system. In further embodiments of the invention, it should be appreciated that a plurality of targets may be positioned on an individual cradle for use in aligning the cradle and the scan plane. For example, in one embodiment, two targets may be positioned on a cradle such that the first target, nearest to the gantry, includes an aperture where the target point is located, and the second target is positioned on the far end of the cradle away from the gantry, so that when properly aligned, the alignment laser beam travels through the crosshair aperture on the first target and intersects the target point on the second target, producing the visible laser dot.

It should also be appreciated that although the invention is shown and described with reference to a single gantry imaging system, the invention may be adapted for use with multiple gantry assemblages. For example, if a patient table is located between two gantries for imaging, the patient table could have at least two targets positioned thereon, one for alignment with each gantry as described above with reference to FIGS. 1–8.

A further embodiment of the invention may employ a target centerline placed down the axis of the cradle. In this embodiment, the alignment of the cradle and the scan plane is verified by intersecting the alignment laser beam down the axis of the cradle as the cradle is translated into the patient bore. Although in this arrangement the alignment laser beam typically is not coaxial with the center axis of the patient bore, the laser dot produced by the alignment laser beam allows the user to determine if the cradle and scan plane are aligned by measuring any distance away from the centerline of the cradle that the laser dot is produced.

As described above with reference to various embodiments of the invention, the imaging system, or various components thereof, may receive input from or send output to a processing machine to accomplish the desired function of the invention. It should be appreciated that the imaging system, or components thereof, may receive commands from a controller workstation through the processing machine, or other mechanical components electronically coupled to or in communication with a processing machine.

As used herein, the term "processing machine" is to be understood to include at least one processor that uses at least one memory. The memory stores a set of instructions. The instructions may be either permanently or temporarily stored in the memory or memories of the processing machine. The processor executes the instructions that are stored in the memory or memories in order to process data. The set of instructions may include various instructions that perform a particular task or tasks, such as those tasks described above. Such a set of instructions for performing a particular task may be characterized as a program, software program, or simply software. As noted above, the processing machine executes the instructions that are stored in the memory or memories to process data. This processing of data may be in response to commands by a user or users of the processing machine, in response to previous processing, in response to a request by another processing machine and/or any other input, for example.

The processing machine used to implement exemplary embodiments of the invention may be a general purpose computer. However, the processing machine described above may also utilize any of a wide variety of other technologies including a special purpose computer, a computer system including a microcomputer, mini-computer or mainframe, a programmed microprocessor, a microcontroller, an integrated circuit, a logic circuit, a digital signal processor, a programmable logic device, or any other device or arrangement of devices that is capable of implementing exemplary embodiments of the invention.

Many embodiments and adaptations of the present invention other than those herein described, will be apparent to those skilled in the art by the foregoing description thereof, without departing from the substance or scope of the invention. While the present invention has been described herein in detail in relation to its exemplary embodiments, it is to be understood that this disclosure is only illustrative and exemplary of the present invention Accordingly, the foregoing disclosure is not intended to limit the scope of the present invention which is defined by the claims and their equivalents.

What is claimed is:

1. For an imaging system including a gantry having a patient bore, and a patient table having a cradle, a method of aligning the cradle with a scan plane in the patient bore, comprising:
    positioning a laser device at least partially within the patient bore, the laser device producing an alignment laser beam projecting along an axis of the patient bore normal to the scan plane; and
    aligning the cradle of the patient table such that when the cradle is translated into the scan plane in the patient bore, the alignment laser beam intersects a positioning target on the cradle.

2. The method of claim 1, wherein the alignment laser beam intersects a target point on the positioning target.

3. The method of claim 1, wherein the alignment laser beam intersects a laser sensing device on the positioning target.

4. The method of claim 3, wherein the laser sensing device is a charge coupled device.

5. The method of claim 1, wherein aligning the cradle with the scan plan further comprises:
    determining an intersection point of the alignment laser beam on the positioning target;
    determining a variance between the intersection point and a target point on the positioning target; and
    adjusting the cradle to align the intersection point and target point.

6. For an imaging system including a gantry having a patient bore, and a patient table having a cradle, a method of aligning the cradle with a scan plane in the patient bore, comprising:
    positioning a laser device at least partially within the patient bore, the laser device producing an alignment laser beam projecting along an axis of the patient bore normal to the scan plane; and
    aligning the cradle of the patient table such that when the cradle is translated into the scan plane in the patient bore, the alignment laser beam intersects a positioning target on the cradle,
    wherein the laser device further produces a plurality of coplanar laser beams perpendicular to the alignment laser beam, each coplanar laser beam intersecting an associated positioning point on a septum.

7. For an imaging system including a gantry having a patient bore, and a patient table having a cradle, a method of aligning the cradle with a scan plane in the patient bore, comprising:
    positioning a laser device at least partially within the patient bore, the laser device producing an alignment laser beam projecting along an axis of the patient bore normal to the scan plane;
    advancing the cradle into the patient bore; and
    repeatedly determining that the alignment laser beam intersects a positioning target on the cradle when the cradle is being advanced into the patient bore.

8. The method of claim 7, further comprising repeatedly determining that the alignment laser beam intersects a target point on the positioning target when the cradle is being advanced into the patient bore.

9. The method of claim 7, further comprising repeatedly determining that the alignment laser beam intersects a laser sensing device on the positioning target.

10. The method of claim 9, wherein the laser sensing device is a charge coupled device.

11. For an imaging system including a gantry having a patient bore, and a patient table having a cradle, a method of aligning the cradle with a scan plane in the patient bore, comprising:
    positioning a laser device at least partially within the patient bore, the laser device producing an alignment laser beam projecting along an axis of the patient bore normal to the scan plane;
    advancing the cradle into the patient bore; and
    repeatedly determining that the alignment laser beam intersects a positioning target on the cradle when the cradle is being advanced into the patient bore, wherein the laser device produces a plurality of coplanar laser beams perpendicular to the alignment laser beam, each coplanar laser beam intersecting an associated positioning point on a septum.

12. The method of claim 11, further comprising repeatedly determining that each coplanar laser beam intersects the associated positioning point on the septum.

13. An imaging system comprising:
   a gantry including a patient bore;
   a patient table including a cradle; and
   a laser device positioned at least partially within the patient bore and configured to produce an alignment laser beam projecting along an axis of the patient bore normal to a scan plane,
   wherein the alignment laser beam is configured to intersect a positioning target on the cradle such that the cradle is normal to the scan plane when the cradle is translated into the patient bore.

14. The imaging system of claim 13, wherein the laser device is positioned at least partially within the patient bore.

15. The imaging system of claim 13, wherein the alignment laser beam is configured to intersect a target point on the positioning target.

16. The imaging system of claim 13, wherein the alignment laser beam is configured to intersect a laser sensing device on the positioning target.

17. The imaging system of claim 16, wherein the laser sensing device is a charge coupled device.

18. An imaging system comprising;
   a gantry including a patient bore;
   a patient table including a cradle; and
   a laser device positioned at least partially within the patient bore and configured to produce an alignment laser beam projecting alone an axis of the patient bore normal to a scan plane,
   wherein the alignment laser beam is configured to intersect a positioning target on the cradle such that the cradle is normal to the scan plane when the cradle is translated into the patient bore, and
   the laser device is configured to produce a plurality of coplanar laser beams perpendicular to the alignment laser beam, each coplanar laser beam configured to intersect an associated positioning point on a septum.

* * * * *